(12) United States Patent
Botros (10) Patent No.: US 8,838,250 B2
(45) Date of Patent: Sep. 16, 2014

(54) CONFIGURING A HEARING PROSTHESIS WITH A REDUCED QUANTITY OF PARAMETERS

(75) Inventor: Andrew Botros, Maroubra (AU)

(73) Assignee: Cochlear Limited, Macquarie University, NSW (AU)

( * ) Notice: Subject to any disclaimer, the term of this patent is extended or adjusted under 35 U.S.C. 154(b) by 150 days.

(21) Appl. No.: 13/365,017

(22) Filed: Feb. 2, 2012

(65) Prior Publication Data
US 2013/0204325 A1 Aug. 8, 2013

(51) Int. Cl.
*A61N 1/36* (2006.01)
(52) U.S. Cl.
USPC .................. 607/57; 607/55; 607/56; 381/60
(58) Field of Classification Search
USPC .................. 607/55–57, 137; 381/60
See application file for complete search history.

(56) References Cited

U.S. PATENT DOCUMENTS

| 8,355,794 B2* | 1/2013 | Lineaweaver et al. .......... 607/57 |
| 2004/0071304 A1 | 4/2004 | Yanz et al. |
| 2007/0076909 A1 | 4/2007 | Roeck et al. |
| 2009/0060214 A1 | 3/2009 | Wessel et al. |
| 2009/0299435 A1* | 12/2009 | Gliner et al. .................... 607/45 |
| 2012/0008809 A1 | 1/2012 | Vandali et al. |

FOREIGN PATENT DOCUMENTS

KR 10-2001-0008008 2/2001

OTHER PUBLICATIONS

International Search Report and Written Opinion for International Application No. PCT/IB2013/050879 mailed Jul. 8, 2013 (9 pages).

* cited by examiner

*Primary Examiner* — Joseph Stoklosa
(74) *Attorney, Agent, or Firm* — K&L Gates LLP (57) ABSTRACT

A method for determining a first set of one or more parameters for configuring a system, the method including evaluating a behavior of the system over a predetermined selection of parameter values for a second set of parameters, and deriving a first set of one or more parameters to configure the system based on the evaluated behavior of the system, wherein the number of parameters in the first set is less than the number of parameters in the second set.

14 Claims, 6 Drawing Sheets

FIG. 6 ively related to a single parameter value change, but, instead often result in the values of multiple parameters being changed. The effect of one parameter value change often depends on the value of another parameter. Alternatively, the effect of changing one or more parameter values may not significantly impact the system's behavior.

CONFIGURING A HEARING PROSTHESIS WITH A REDUCED QUANTITY OF PARAMETERS

BACKGROUND

1. Field of the Invention

The present invention relates generally to a hearing prosthesis, and more particularly, to configuring a hearing prosthesis with a reduced quantity of parameters.

2. Related Art

Complex systems often have a large number of input variables or parameters ("parameters" herein) that specify the system's operation. Configuration of these parameters can be time consuming, particularly when each parameter has a wide range of possible values ("parameter values" herein). Additionally, state changes in such systems are often not simply related to a single parameter value change, but, instead often result in the values of multiple parameters being changed. The effect of one parameter value change often depends on the value of another parameter. Alternatively, the effect of changing one or more parameter values may not significantly impact the system's behavior.

In complex system's involved in the treatment or prevention of a medical condition or disability, configuration of the system may be further complicated by the availability and ability of a human subject to evaluate the system's performance. One such system is a cochlear implant, which converts external stimuli in the form of acoustic sound into a sequence of electrical stimuli that are applied to electrodes implanted within a recipient's cochlea. Cochlear implants typically have a large number of parameters that are involved in converting the acoustic sound into electrical stimuli. The specific values for these parameters may have a significant impact on the sound perceived by the recipient; and, the impact of changes in different parameter values may have different effects for different recipients. The process of configuring (i.e., determining the values of the parameters for a recipient) a cochlear implant is commonly referred to as a "fitting" and the parameters are commonly collectively referred to as the MAP.

SUMMARY

According to an exemplary embodiment, there is a method for determining a first set of one or more parameters for configuring a system, the method comprising evaluating a behavior of the system over a predetermined selection of parameter values for a second set of parameters, and deriving a first set of one or more parameters to configure the system based on the evaluated behavior of the system, wherein the number of parameters in the first set is less than the number of parameters in the second set.

According to another exemplary embodiment, there is a method of reducing the input variables for configuring a medical implant that stimulates a physiological system according to external stimuli, the medical implant including a sensor to generate a sensed signal in accordance with the external stimuli, a processor for processing the sensed signal to generate a stimulation signal, the processor configured by a plurality of input variables adopting associated parameterization values, a stimulator for stimulating the physiological system in accordance with the stimulation signal, the method including evaluating by a recipient a behavior of the medical implant over a predetermined selection of the parameterization values and deriving one or more new derived input variables to configure the medical implant based on the behavior of the medical implant as determined by the recipient, wherein the total number of the one or more new input variables is less than the number of input variables.

BRIEF DESCRIPTION OF THE DRAWINGS

Illustrative embodiments of the present invention will be discussed with reference to the accompanying drawings wherein.

DETAILED DESCRIPTION

Before describing the configuration method in detail, it is convenient to describe the operation of a cochlear implant system.

Embodiments of the present invention are described herein primarily in connection with one type of hearing prosthesis, namely a cochlear prostheses (commonly referred to as cochlear prosthetic devices, cochlear implants, cochlear devices, and the like; simply "cochlea implants" herein.) Cochlear implants generally refer to hearing prostheses that deliver electrical stimulation to the cochlea of a recipient. As used herein, cochlear implants also include hearing prostheses that deliver electrical stimulation in combination with other types of stimulation, such as acoustic or mechanical stimulation. It would be appreciated that embodiments of the present invention may be implemented in any cochlear implant or other hearing prosthesis now known or later developed, including auditory brain stimulators, or implantable hearing prostheses that acoustically and/or mechanically stimulate components of the recipient's middle or inner ear. Further, while the below embodiments, will be discussed with reference to configuring a cochlear implant, it should be appreciated that embodiments of the present invention will have applications to other multiple input systems.

Figure 1:
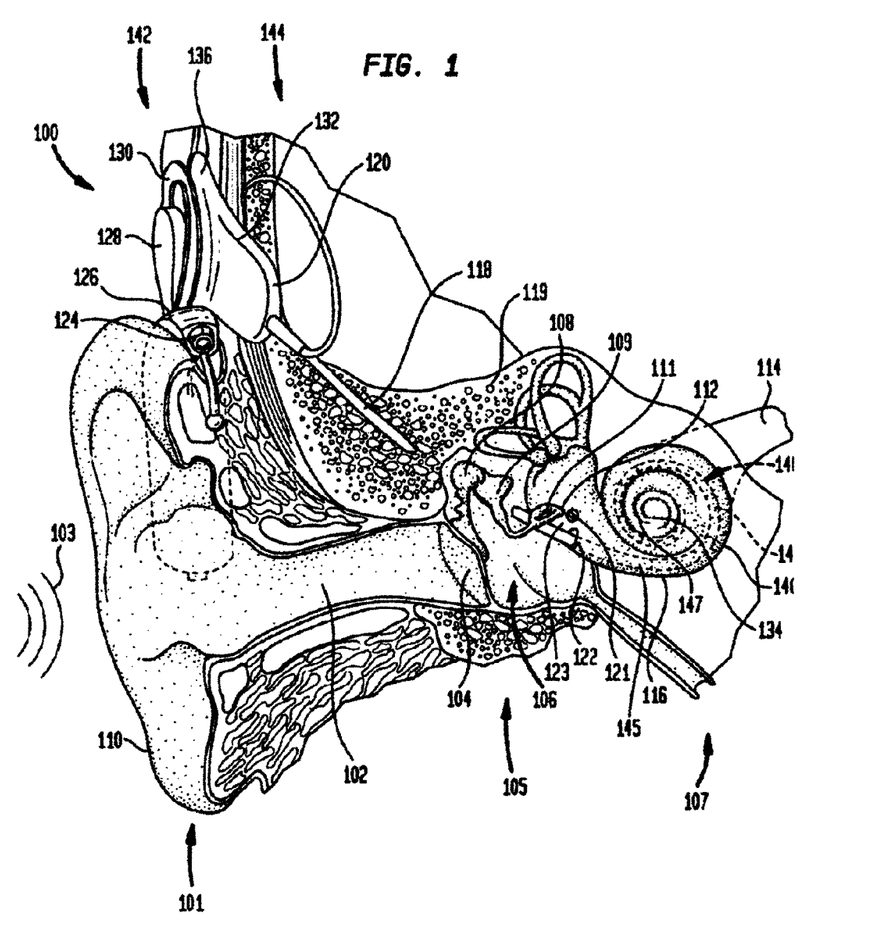
FIG. 1 depicts an exemplary hearing prosthesis in the form of a cochlear implant, which may be fitted utilizing embodiments of the present invention.

FIG. 1 is a perspective view of an exemplary cochlear implant 100 implanted in a recipient having an outer ear 101, a middle ear 105, and an inner ear 107. Components of outer ear 101, middle ear 105, and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear cannel 102 is a tympanic membrane 104 that vibrates in response to sound wave 103. This vibration is coupled to oval window or fenestra ovalis 112 through three bones of middle ear 105, collectively referred to as the ossicles 106 and comprising the malleus 108, the incus 109, and the stapes 111. Bones 108, 109, and 111 of middle ear 105 serve to filter and amplify sound wave 103, causing oval window 112 to articulate, or vibrate, in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

Cochlear implant 100 comprises an external component 142 that is directly or indirectly attached to the body of the recipient, and an internal or implantable component 144 that is temporarily or permanently implanted in the recipient.

External component 142 typically comprises one or more sound input elements, such as microphone 124 for detecting sound, a sound processing unit 126, a power source (not shown), and an external transmitter unit 128. External transmitter unit 128 comprises an external coil 130, and, by way of example, a magnet (not shown) secured directly or indirectly to external coil 130. Sound processing unit 126 processes the output of microphone 124 that is positioned, in the depicted embodiment, by auricle 110 of the recipient. Sound processing unit 126 generates encoded signals, sometimes referred to herein as encoded data signals, which are provided to external transmitter unit 128 via a cable (not shown).

Internal component 144 comprises an internal receiver unit 132, a stimulator unit 120, and an elongate stimulating lead assembly 118. Internal receiver unit 132 comprises an internal coil 136, and by way of example, a magnet (also not shown) fixed relative to the internal coil. Internal receiver unit 132 and stimulator unit 120 are hermetically sealed within a biocompatible housing, sometimes collectively referred to as a stimulator/receiver unit. Internal coil 136 receives power and stimulation data from external coil 130, as noted above. Elongate stimulating lead assembly 118 has a proximal end connected to stimulator unit 120, and extends through mastoid bone 119. Lead assembly 118 has a distal region, referred to as electrode assembly 145, implanted in cochlea 140. As used herein the term "stimulating lead assembly," refers to any device capable of providing stimulation to a recipient, such as, for example, electrical or optical stimulation.

Electrode assembly 145 may be implanted at least in basal region 116 of cochlea 140, and sometimes further. For example, electrode assembly 145 may extend towards apical end of cochlea 140, referred to as cochlea apex 134. Electrode assembly 145 may be inserted into cochlea 140 via a cochleostomy 122, or through round window 121, oval window 112, and the promontory 123 or opening in an apical turn 147 of cochlea 140.

Electrode assembly 145 has disposed therein or thereon a longitudinally aligned and distally extending array 146 of electrode contacts 148, sometimes referred to as electrode array 146 herein. Throughout this description, the term "electrode array" means a collection of two or more electrode contacts, sometimes referred to simply as contacts herein. As used herein, electrode contacts or other elements disposed in a carrier refer to elements integrated in, or positioned on, the carrier member. As such, electrode array 146 is referred to herein as being disposed in electrode assembly 145. Stimulator unit 120 generates stimulation signals which are applied by electrodes 148 to cochlea 140, thereby stimulating auditory nerve 114.

In cochlear implant 100, external coil 130 transmits electrical signals (i.e., power and stimulation data) to internal coil 136 via a radio frequency (RF) link. Internal coil 136 is typically a wire antenna coil comprised of multiple turns of electrically insulated single-strand or multi-strand platinum or gold wire. The electrical insulation of internal coil 136 is provided by a flexible silicone molding (not shown). In use, implantable receiver unit 132 may be positioned in a recess of the temporal bone adjacent auricle 110 of the recipient.

As noted, FIG. 1 illustrates a context of the present technology in which cochlear implant 100 includes an external component 142. It would be appreciated that in alternative embodiments, cochlear implant 100 comprises a mostly-implantable or totally implantable device. A totally implantable prosthesis that is capable of operating, at least for a period of time, without the need of an external component. In such embodiments, all components of cochlear implant 100 are implantable, and the cochlear implant operates in conjunction with external component 142.

Because recipients are heterogeneous, each recipient of a cochlear implant may be provided with a different set of parameters to maximize speech reception and recipient satisfaction. A clinical professional, usually an audiologist, typically selects a set of parameters, commonly referred to as a parameter map or, more simply, a MAP, that will provide the best possible sound reception for an individual recipient during a process commonly referred to as fitting the cochlear implant. Once determined, the MAP is typically stored in the sound processor of the cochlear implant and used for processing received audio signals and applying the corresponding stimulation to the recipient.

The first step in fitting a cochlear implant to a recipient typically involves setting the T and C levels (threshold and comfort levels, respectively) for each electrode and/or stimulation channel of the cochlear implant. For example, a cochlear implant may be configured to provide one stimulation channel for each electrode contact 148 of cochlear implant 100, or, in other embodiments the number of stimulation channels may not match the number of electrodes, and each stimulation channel may use one or more of electrode contacts in applying stimulation. Threshold levels are comparable to acoustic threshold levels; and, comfort levels indicate the level at which a sound is loud but comfortable. After determining the T and C levels, the fitting process typically involves determining the other values of the parameters in the MAP.

As an example of the type and number of MAP parameters employed in a cochlear implant, the Advanced Combination Encoder (ACE) processing strategy that is implemented in the NUCLEUS FREEDOM system commercially available from Cochlear Ltd. employs 10 or more MAP parameters (apart from the T and C levels per electrode), with some of the more prominent parameters being:

Per-channel stimulation rate: The rate (in Hz) at which biphasic pulses are output on any single electrode;

Number of spectral maxima: The number of electrodes that are stimulated within any given sound processing epoch (the epoch duration is the reciprocal of the per-channel stimulation rate);

Sensitivity: A dimensionless setting that determines the input operating range (minimum and maximum acoustic input) of the sound processor-higher values have lower minimum and maximum input levels, i.e. more sensitive;

T-SPL: The minimum acoustic input (in dB sound pressure level (SPL)) that is mapped to electrical output on a electrode (at T level); and Loudness growth: A dimensionless setting that determines the shape of the acoustic input to electrical output function.

The ACE processing strategy is described in Vandali, A. E., Whitford, L. A., Plant, K. L. & Clark, G. M., "Speech perception as a function of electrical stimulation rate: using the Nucleus 24 cochlear implant system," *Ear & Hearing* 21 (6):608-624 (2000); and Plant, K. L., Whitford, L. A., Psarros, C. E. 7 Vandali, A. E., "Parameter selection and programming recommendations for the ACE and CIS speech-processing strategies in the Nucleus 24 cochlear implant system," *Cochlear Implants International* 3 (2):104-125 (2002).

Even though the above list of parameters is only a subset of the MAP parameters available to a clinician in configuring a cochlear implant, it would be readily appreciated by those of ordinary skill in the art that the total number of combinations of values for the MAP parameters may be extremely large (in the billions), making the configuration of the device extremely complex and time consuming if an exhaustive search over the entire set of MAP parameters (commonly referred to as the parameters space) is conducted.

Accordingly, when fitting a cochlear implant to a recipient, clinicians adopt a variety of approaches or technologies. Some will simply employ a standard combination of values for each MAP parameter for all recipients. Others, may choose different MAPs according to the recipient's age or other indicators. Other clinicians will attempt to vary the parameter values as part of the fitting process, basing their change in a given value on recipient feedback. Even in this latter case, parameters may interact significantly with each other, and thus determining which parameter to adjust is not always readily apparent.

A further complication is that many MAPs are sometimes perceived to be very similar by a recipient. This may be due to two reasons: (i) a given MAP parameter may have little influence on the sound quality as perceived by the recipient; and (ii) multiple MAP parameters may influence sound quality through similar mechanisms, or strongly interact. This also makes it difficult to employ a systematic search for the MAP that will provide the optimal performance for an individual recipient.

In the below discussed exemplary description, the MAP for cochlear implant 100 will be assumed to include the five adjustable input parameters listed in Table A along with their associated range of values. It should be noted, however, these parameters and their values are exemplary only. Further, in the discussed embodiment, the MAP will be assumed to be stored by sound processor 126 (FIG. 1).

TABLE A

MAP PARAMETERS FOR COCHLEAR IMPLANT 100

| Parameter (Input Variable) | Name | Minimum Value | Maximum Value |
|---|---|---|---|
| $P_1$ | Per-channel stimulation rate | 250 Hz | 4000 Hz |
| $P_2$ | Number of spectral minima | 1 | 10 |
| $P_3$ | Sensitivity | 0 | 20 |
| $P_4$ | T-SPL | 10 dB | 50 dB |
| $P_5$ | Loudness Growth | 10 | 50 |

Figure 2:
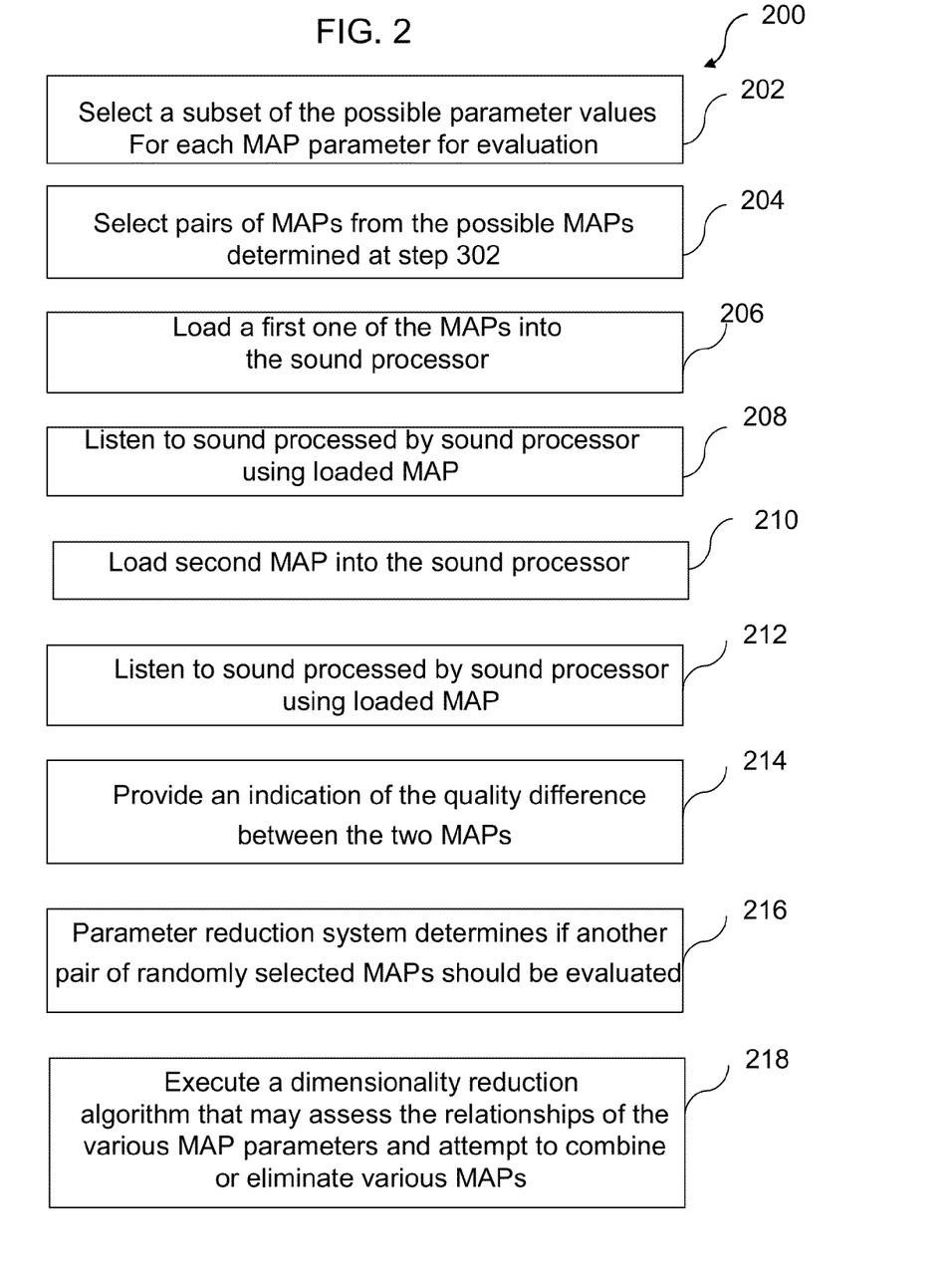
FIG. 2 is an exemplary method according to an exemplary embodiment.

FIG. 2 is a flowchart of an exemplary method 200 for configuring a cochlear implant, in accordance with an embodiment of the invention. In the discussed embodiment, the MAP will be defined as follows:

$$M \equiv [V_{P1}, V_{P2}, V_{P3}, V_{P4}, V_{P5}],$$

where $V_{Pk}$ is the value for parameter $P_k$.

As noted, above the values for the parameters $P_1$ through $P_5$ may range between the listed minimum and maximum values and have any value within this range. Thus, there is an extremely large number of possible combinations of parameter values. In the presently discussed embodiment, an audiologist or other individual, at step 202, selects a subset of the possible parameter values for each MAP parameter for evaluation. This subset of MAP parameter values may be chosen, for example, so that the range of parameter values sufficiently spans the possible range of possible parameter values. For example, in an embodiment, the minimum and maximum values for each parameter are included in this subset along with one or more values distributed between these minimum and maximum values.

The audiologist may store this selection in a computer or other device (hereinafter referred to as "the parameter reduction system") configured for use in performing the method of FIG. 3. This parameter reduction system may, for example, be a general purpose computer programmed for use in performing the method of FIG. 3, or, for example, a device specifically designed for use in performing the method of FIG. 3.

Table B provides a set of exemplary parameter values chosen for each of the five parameters of Table A. As shown, these values include the minimum and maximum value for each parameter along with at least one value between the minimum and maximum values.

TABLE B

SELECTED PARAMETERIZATION VALUES

| Parameter (Input Variable) | Name | Values |
|---|---|---|
| $V_{P1}$ | Per-channel stimulation rate | 250, 500, 1000, 2000 and 4000 HZ |
| $V_{P2}$ | Number of spectral minima | 4, 6, 8, and 10 |
| $V_{P3}$ | Sensitivity | 5, 10 and 15 |
| $V_{P4}$ | T-SPL | 15, 25, and 35 |
| $V_{P5}$ | Loudness Growth | 20, 30 and 40. |

Using the subset of parameter values listed in Table B still provides 540 unique MAPS:

$$M_1 \equiv [V_{P1}=250, V_{P2}=4, V_{P3}=5, V_{P4}=15, V_{P5}=20]$$

$$M_2 \equiv [V_{P1}=500, V_{P2}=4, V_{P3}=5, V_{P4}=15, V_{P5}=20]$$

...

$$M_{540} \equiv [V_{P1}=4000, V_{P2}=10, V_{P3}=15, V_{P4}=35, V_{P5}=40]$$

Although the reduction of possible values for the MAP parameters in step 202 significantly reduces the number of MAPS to be evaluated, it still remains a significant number (540) that would still be prohibitive if each MAP were evaluated in fitting it a cochlear implant to a recipient. Moreover, if each possible MAP were to compared to each other possible MAP, this would require 145,530 comparisons ($^{540}C_2$=145,530).

At step 204, the parameter reduction system randomly selects pairs of MAPs from the possible MAPs determined at step 202. These MAPs are then compared, at blocks 206-216, to evaluate the differences in performance of cochlear implant 200. This pair of MAPs may compared to each other by, for example, having each of one or more recipients to listen to sound processed (by sound processor 126) using each MAP in a typical sound environment and providing a measure of the perceived sound quality difference between the MAPs. For example, in an embodiment, the parameter reduction system may load a first one of the MAPs into the sound processor 126 (FIG. 1) at step 206. This MAP may be loaded into the sound processor by, for example, connecting the parameter reduction system and sound processor 126 using, for example, wired or wireless interfaces included in the parameter reduction system and sound processor, respectively.

The recipient may then listen to sound, at step 208 that is processed by sound processor 126 using the loaded MAP. Different types of sound may be presented to the recipient at step 208. For example, in an embodiment, the audiologist may simply talk to the recipient after the MAP is loaded. Or, for example, in another embodiment, a sample of recorded sound (e.g., a child's voice in a playground) may be played by the parameter reduction system for the recipient to evaluate.

Then, parameter reduction system loads the second MAP into the sound processor 126 at step 210. The recipient may then listen to sound processed by the sound processor 126 using this second MAP at step 212. This sound may be the same sound or same type of sound used at step 208.

After the recipient listens to sound processed by each MAP, the recipient may then provide an indication of the quality difference between the two MAPs at step 214. For example, the recipient may be asked to rank on a scale of 0 to 5 the difference in quality between the two MAPs, where 0 indicates no perceived difference and 5 indicates a significant difference in quality. This perceived quality difference may be stored by the audiologist in a computer, or other device configured for use in performing the method of FIG. 3. For example, this perceived quality difference may be stored in a sound quality difference matrix. An exemplary sound quality difference matrix is discussed below with reference to FIG. 3.

After recording the perceived quality difference, the parameter reduction system determines if another pair of randomly selected MAPs should be evaluated at step 216. If so, the process returns to step 204. In an embodiment, the parameter reduction system may, for example, evaluate a specific number of randomly selected MAP pairs (e.g, 1000 comparisons). As would be appreciated by those of ordinary skill in the art, there will be a tradeoff between the number of random MAPs pairs evaluated and the characterization of the behavior of cochlear implant 100.

If at step 216, the process determines not further evaluate MAP pairs, the process executes, at step 218, a dimensionality reduction algorithm that may assess the relationships of the various MAP parameters and attempt to combine or eliminate various MAPs. A description of exemplary dimensionality reduction algorithms is presented below. As used herein, the term dimensionality reduction algorithm refers to any process capable of reducing the number of dimensions of a multi-dimensional space to spaces. Exemplary dimensionality reduction algorithms that will be discussed in more detail below include processes that use the Multi-dimensional Scaling (MDS) technique and the Principal Components Analysis (PCA) technique. These techniques, for example, exploit redundancy in the original parameter space (e.g., the original five parameters define a five dimensional parameter space) to reduce the number of dimensions of the space, such that the cochlear implant may be configured using this reduced dimensional space.

Figure 3:
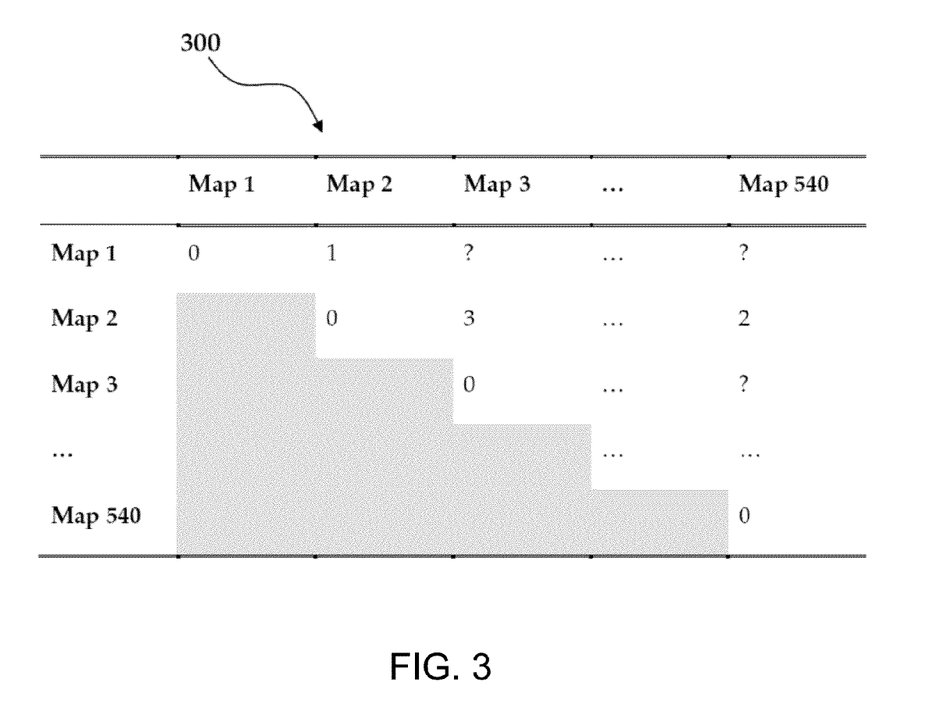
FIG. 3 is a table depicting the measured sound quality differences between different MAP combinations.

FIG. 3 provides an exemplary sound quality difference matrix 300 that may be used for recording the evaluations of the MAP pair, in accordance with an embodiment of the invention. In the illustrated matrix 300 only a subset of the possible MAP pairs have been evaluated, with the vast majority of pairs not evaluated (these pairings being denoted by a question mark, "?." However, the quantity of MAPs that are selected to be evaluated data is sufficient such that the parameter reduction system may be able to make determinations about the interactions of the parameters. For simplicity, the bottom left portion of the matrix 300 is shaded. This portion of the matrix would be a mirror reflection of the values in the top right portion. That is, the quality difference evaluation of MAPs 1 and 2 is the same as the quality difference evaluation of MAPs 2 and 1.

In another embodiment, rather than evaluating random pairs of MAPs, the parameter reduction system may randomly select a reference MAP and two other MAPs (collectively referred to as a triplet of MAPs). Each MAP may be loaded into the sound processor 126 and sound presented to the recipient. The recipient may then indicate which of the two MAPs sound most like the reference MAP.

Referring back to FIG. 2, as noted above, a dimension reduction algorithm may be used at step 218. In an embodiment, the parameter reduction system may use a dimensionality reduction algorithm that analyzes the obtained evaluations (step 214) to assess the relationships between the MAP parameters. For example, in an embodiment, the parameter reduction system may use a multidimensional scaling (MDS) algorithm to analyze the obtained evaluations to assess the relationships of the various parameters (e.g., the similarities/distance between the various parameters). Multidimensional scaling (MDS) is a set of related statistical techniques employed to explore similarities or dissimilarities between input variable (e.g., the MAP parameters), and which then assigns a location to each item in N-Dimensional space, where N may be specified a priori by, for example, the system designer or other person. The general MDS technique is described in Kruskal, J. B. & Wish, M., *Multidimensional Scaling*, Sage University Paper Series on Quantitative Applications in the Social Sciences, 07-011, Sage Publications (1978); and Cox, T. F. & Cox, M. A. A. *Multidimensional Scaling* (second edition), Monographs on Statistics and Applied Probability, 88, CRC Press (2000).

In embodiments in which the recorded evaluations at step 214 (FIG. s) are comparisons of pairs of MAPs, such as discussed above with reference to FIG. s, the parameter reduction system may use a metric-MDS algorithm is assessing the relationships of the various parameters. A metric-MDS algorithm is a superset of MDS algorithms that is based on measured distances. In other embodiment, in which the recorded evaluations are comparisons of three MAPs (e.g., where a reference MAP is compared to two other MAPs as described above), the parameter reduction system may use a non-metric MDS algorithm in assessing the relationships of the various parameters.

In assessing the relationships of the various MAP parameters, the MDS algorithm attempts to preserve the sound quality differences or "distances" by placing the MAPs appropriately within a specified number of dimensions. This process also provides an overall error in "distance" or sound quality difference between the MAPs by which the level of dimensionality can be assessed based on this goodness of fit. It should be noted that the dimensions themselves are arbitrary. This process examines the underlying dimensionality of the data by systematically modifying the number of dimensions and applying the MDS algorithm. A data analyst is able to assess the inherent dimensionality by monitoring the distance error. This dimensionality found by the MDS algorithm defines a new parameter space, where each dimension of this new parameter space defines a new a parameter. In some embodiments, additional techniques are then employed to find a relationship between the original parameters and the new parameters defined by the dimensionality of the new parameter space.

Referring back to Tables A and B, in the presently discussed embodiment, the MAP comprises 5 parameters, $M \equiv [V_{P1}, V_{P2}, V_{P3}, V_{P4}, V_{P5}]$. For illustrative purposes, in the following description it will be assumed that the method of FIG. s is applied followed by application of an MDS algorithm to the stored evaluations. It will further be assumed that the MDS algorithm results in an assessment that the MAPs may be placed in a two-dimensional parameter-space where the overall error between the two-dimensional parameter-space and the recorded evaluations is small. This implies that the perceived sound quality of cochlear implant 100 may be configured using two new parameters (one for each dimension of the two-dimension parameter space) rather than the original five parameters.

In an embodiment, rather than varying the five original parameters in fitting cochlear implant 100, the audiologist (or fitting system) may simply vary these two new parameters in attempting to derive the optimal MAP for the recipient. The parameter reduction system may MAP the two new parameters to the original parameters. Thus, in fitting the cochlear implant, the audiologist (or fitting system, if used) may simply vary these two new parameters. The fitting system may then map the values for these two parameters to the five original parameters to determine the MAP corresponding to these two new parameter values. The MAP may then be provided to the speech processor 126 (FIG. 1) for purposes of enabling the recipient to evaluate the MAP. Thus, in the present embodiment, only two variables (i.e., the two new parameters) are adjusted, rather than all five parameters, in fitting the cochlear implant 100.

As used herein, the term fitting system refers to any combination of hardware and/or software configured for use in fitting a cochlear implant to a recipient. For example, a fitting system my comprise an interface through which the fitting system may be connected to speech processor 126 (FIG. 1) through which the fitting system may download MAPs to speech processor 126. The fitting system may further comprises a user interface such as for example, as keyboard and mouse along with a display for use by the audiologist in fitting the cochlear implant.

As noted above, in the present embodiment, N=2. Thus, the dimension reduction algorithm of the present embodiment maps the 5 dimensional MAP space to two dimensions, represented as Dim1 and Dim2, respectively. Further, in this illustrative example, it is assumed that it is known that the $P_1$ (Per-channel stimulation rate) and $P_2$ (Number of spectral minima) parameters are highly related and that this relationship may be represented by a Total Stimulation Rate (TSR) parameter that acts as an independent influence on sound quality, where TSR is defined as the per-channel stimulation rate ($P_1$) multiplied by the number of spectral maxima ($P_2$) or:

$$TSR = V_{P1} V_{P2}$$

The correlation between this new parameter, TSR, and the two-dimensions of the parameter-space may be calculated, by for example, calculating a Pearson correlation coefficient between TSR and the location of the maps along each of the two dimensions. Each map provides a single data point for the correlation calculation. In this example, it is assumed the calculated correlation coefficient for the first dimension $r_{Dim1}$ is equal to 0.94 and the correlation coefficient for the second dimension $r_{Dim2}$ is equal to 0.17, where a correlation coefficient of 1.0 means the two variables are perfectly correlated and a correlation coefficient of 0.0 means the two variables are completely uncorrelated. Because, $r_{Dim1}$ (0.94) indicates that TSR is closely correlated with the first dimension, in this example, the first dimension is set to:

$$Dim1 = TSR$$

As such, for a given value of TSR the value of $V_{P1}$ and $V_{P2}$ can range accordingly as defined by the relationship $V_{P1} V_{P2}$.

The parameter reduction system may further perform a multiple regression analysis with the remaining three input variables $V_3$, $V_4$, and $V_5$ which finds a high correlation coefficient ($r_{Dim2}$=0.96) for the following functional dependence:

$$Dim2 = 1.45 + (0.47 \cdot V_3) - (1.44 \cdot V_4) - (2.82 \cdot V_5)$$

It should be noted that the above provides merely one illustration demonstrating how input variables ($V_{P1}$, $V_{P2}$, $V_{P3}$, $V_{P4}$, $V_{P5}$) may be associated with a set of dimensions (Dim1, Dim2), and in other embodiments, other techniques may be used for associating a set of input variables with a target value (e.g., the location of the map in a new dimension). A prior understanding of the MAP parameter interactions (as was exploited by using the TSR parameter above) is not essential. These other techniques for establishing these associations are drawn from the fields of statistics, data mining and machine learning, amongst others. A wide survey of these fields is given in: Han, J. & Kamber, M., *Data Mining: Concepts and Techniques* (second edition), The Morgan Kaufmann Series in Data Management Systems (2006); and Morgan Kaufmann and Mitchell T. M., *Machine Learning*. McGraw-Hill (1997).

In another embodiment, rather than using an MDS algorithm, at step 218 (FIG. 2) for reduction other techniques may be used for reducing the number of parameters to be evaluated during the fitting process. For example, in an embodiment, the evaluation data recorded at step 214 (FIG. 2) may be analyzed using a principal components analysis (PCA). A PCA transforms multidimensional data to a new coordinate system such that the greatest variance along any dimension in the data lies lie on the first coordinate (called the first principal component), the second greatest variance on the second coordinate, and so on. A PCA can be used for reducing the number of dimensions of a multi-dimensional space by keeping lower-order principal components and ignoring higher-order ones. That is, a PCA can be used to transform a number of possibly correlated variables into a smaller number of uncorrelated variables called principal components. As with the MDS algorithm derived previously, the new coordinates obtained from the PCA are then functionally associated with the original parameters.

Although the above-discussed embodiments use a dimensionality reduction algorithm, in another embodiment, the number of dimensions of the parameter space may be reduced by manually observing the behavior or the cochlear implant system 100 over a range of parameter values for the parameters and noting which input variables are significant in causing the behavior of system 100 to change. For example, in an embodiment, the new parameters may simply be a reduced subset of the original parameters. The particular dimensionality reduction technique used does not change the purpose of the invention: that of reducing a system's number of input parameters by exploiting redundancy in these input parameters in the context of the system to allow simpler configuration of that same system.

In an embodiment, a specific perceptual characteristic (e.g. brightness, or clarity) of cochlear implant system 100 may be associated with one of the new input variables (e.g., the new variables determined at step 218 of FIG. 2). To achieve this, a recipient creates a separate sound quality difference matrix for each characteristic, and the dimensionality reduction process is repeated for each characteristic. Thus, with a more detailed analysis it is found that Dim1 is closely associated with brightness, while Dim2 is closely associated with clarity.

In an embodiment, cochlear implant 100 may comprise a controller that may enable a recipient to adjust the new parameters (e.g., brightness and clarity). This controller may enable the recipient to adjust the parameters in real-time (e.g., after completion of the fitting process), such as, for example, based on the current acoustic environment.

Figure 4:
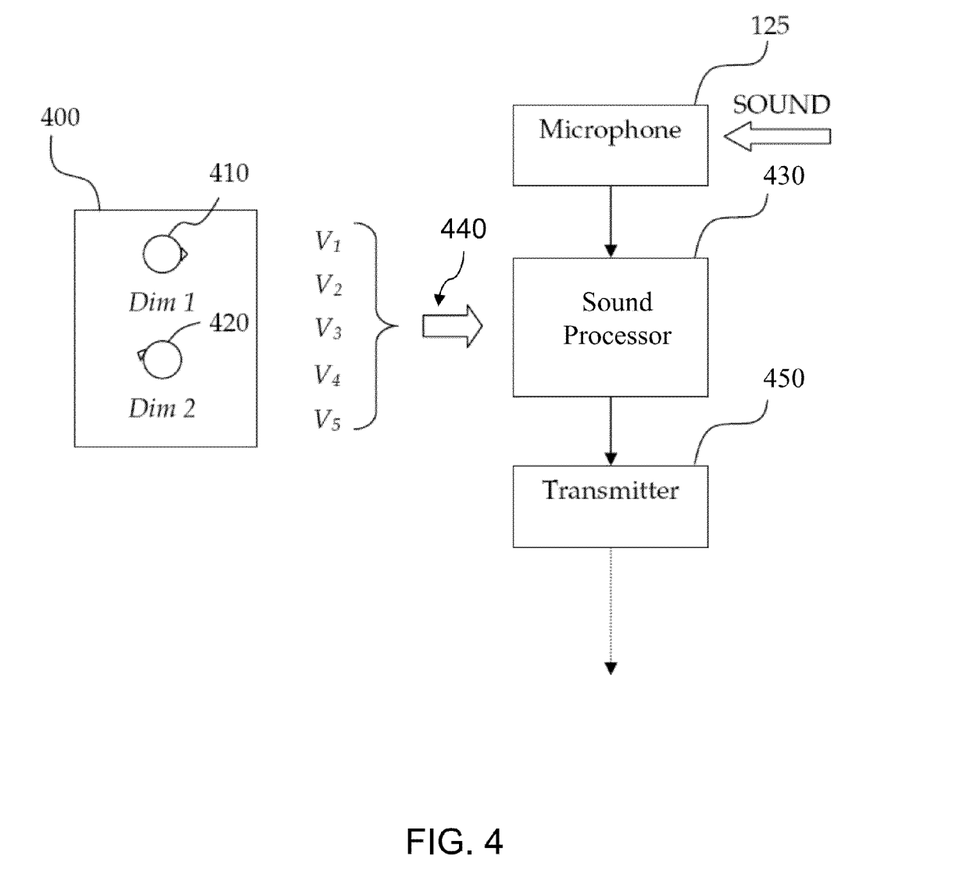
FIG. 4 depicts a configuration device according an illustrative embodiment of the present invention.

FIG. 4 illustrates an exemplary controller 400, in accordance with an embodiment of the present invention. As illustrated, controller 400 comprises two adjustable controls 410 and 420 that correspond to the new input variables Dim1 and Dim2, respectively. A user (e.g., the recipient) may adjustment these new input variables using controls 410 and 420. The position of controls 410 and 420 may be provided to a processor 430 which may correspond to the speech processor 126 and which receives signals from microphone 125 that may determine the values of Dim1 and Dim2 based on the positions of controls 410 and 420 and translate these values for Dim1 and Dim2 to the values of $V_{P1}$, $V_{P2}$, $V_{P3}$, $V_{P4}$, and $V_{P5}$. The processor may then transmit these values ($V_{P1}$, $V_{P2}$, $V_{P3}$, $V_{P4}$, and $V_{P5}$) to sound processor 430 via interface 440. Processor 410 may be, for example, any combination of hardware and/or software. Interface 440 may be, for example, a wired or wireless interface for communicating with sound processor 430. In other embodiments, controller 400 may comprise a computer input display or other control mechanism enabling the recipient to tune or configure sound processor 430. The processed speech from sound processor 430 is then communicated to transmitter 450.

Figure 5:
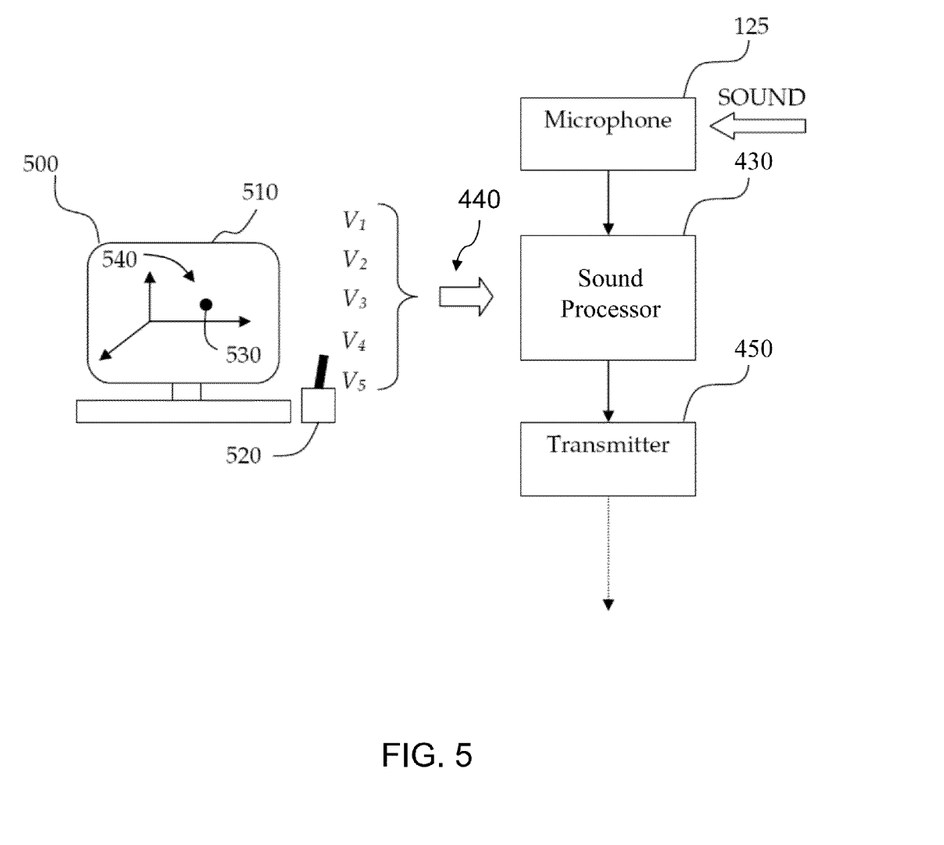
FIG. 5 depicts a configuration device according an illustrative embodiment of the present invention.

FIG. 5 illustrates an exemplary controller 500 for controlling three derived input variables that are operative to configure cochlear implant system 100, in accordance with an embodiment of the present invention. In this illustrative embodiment, controller 500 comprises a computer input display 510 and a joystick 520 or other suitable navigation means such as a track ball and/or keyboard. A recipient uses joystick 520 to navigate or manipulate a cursor 530 through a three dimensional diagram 540 depicted on display 510 as a way of adjusting the three derived input variables (Dim1, Dim2, and Dim3). Controller 500 may translate the values for these three input variable to corresponding original variable values $V_{P1}$, $V_{P2}$, $V_{P3}$, $V_{P4}$ and $V_{P5}$. In operation, this may involve a recipient listening to speech and/or music being played continuously and the recipient then moving through the displayed diagram 540 to dynamically reconfiguring sound processor 430

Figure 6:
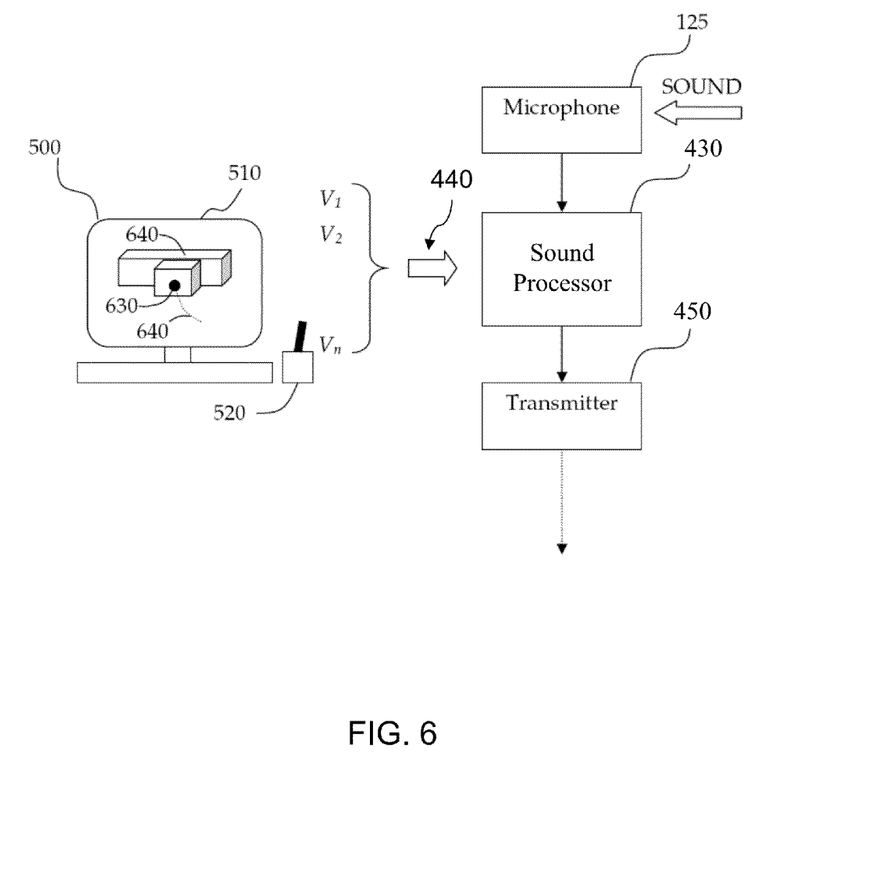
FIG. 6 depicts a configuration device according to yet a further illustrative embodiment of the present invention.

FIG. 6 illustrates yet another exemplary controller 600, in accordance with an embodiment of the invention. In this exemplary embodiment, the number of original input variables may large and the number of derived input variables may be reduced but still large. Controller 600 may enable the recipient to move through a series of three dimensional rooms 640 each corresponding to a set of three parameters. In this embodiment, once a recipient has navigated via cursor 630 to the optimum location for a given room i.e. corresponding to the optimum value for the corresponding three parameters, the recipient will then enter a new room corresponding to a new set of parameters.

In further embodiment, the new room may correspond to a selection of new parameters and old parameters and/or alternatively to a new combination of old parameters for further fine tuning. Furthermore, the path 640 that a recipient traverses to the optimum location may be tracked to determine which further parameters make up the next room. In this manner, a recipient will be able to select a set of multiple derived input variables by navigating a multidimensional space decomposed into three dimensional rooms.

Although the above-discussed embodiments were discussed with reference to a cochlear implant, in other embodiments the above-discussed methods and systems may be applied to a general system that depends on a number of input variables for configuration as part of the initial system development. As a result, the number of input variables may be reduced in a process that can be completed before release of the system to the market.

An alternative system for which the present invention can apply is an image processing system. Image processing systems (typically software systems) offer numerous controls that modify a gen image, such as contrast, brightness, gamma and sharpness. A number of such controls employ overlapping processes; for example, many operations first apply a low-pass filter to the given image, or intensify the color value of each pixel. Thus, simpler image processing software can be created by reducing the number of controls to a new set that achieve the bulk of possible effects. In such a system, for example, brightness and contrast can be combined into a single parameter.

In view of the above, it will be understood that an exemplary embodiment provides a method for reducing the input variables required to configure a system, the system configured by the input variables adopting associated parameterization values to define a state of the system, the method including the following steps: evaluating a behavior of the system over a predetermined selection of parameterization values; and deriving one or more new derived input variables to configure the system based on the behavior of the system, wherein the total number of the one or more new input variables is less than the number of input variables.

In some embodiments, the step of evaluating includes selecting a plurality of discrete parameterization values spanning an input parameterization value range for each input variable, forming a map by selecting a discrete parameterization value for each input variable to form a total set of discrete parameterization values, and measuring a characteristic of the system for the map. In some embodiments, the step of forming the map includes randomly selecting at least one of the discrete parameterization values.

In some embodiments, the steps of forming a map and measuring are carried out a first and second time and compared to each other or to a reference map to form a comparison measure. In an exemplary embodiment, deriving one or more new input variables is based on the comparison measure. In some embodiments, the step of deriving includes a dimensionality reduction algorithm. In some embodiments, the dimensionality reduction algorithm is a multidimensional scaling (MDS) algorithm. In some embodiments, the method further includes the step of associating the one or more derived input variables with the input variables.

In some embodiments, the step of associating includes determining a functional relationship between each of the one or more derived input variables and the input variables. In some embodiments, the method further includes the step of associating the one or more derived input variables with a measured characteristic of the system. In a second aspect the present invention accordingly provides a method of reducing the input variables for configuring a medical implant that stimulates a physiological system according to external stimuli, the medical implant including a sensor to generate a sensed signal in accordance with the external stimuli, a processor for processing the sensed signal to generate a stimulation signal, the processor configured by a plurality of input variables adopting associated parameterization values, a stimulator for stimulating the physiological system in accordance with the stimulation signal, the method including evaluating by a recipient a behavior of the medical implant over a predetermined selection of the parameterization values, deriving one or more new derived input variables to configure the medical implant based on the behavior of the medical implant as determined by the recipient, wherein the total number of the one or more new input variables is less than the number of input variables.

In some embodiments, the step of evaluating includes electing a plurality of discrete parameterisation values spanning an iput parameterization value range for each input variable, forming a map by selecting a discrete parameterization value for each input variable to form a total a set of discrete parameterization values, and measuring a characteristic of the medical implant for the map. In some embodiments, the step of forming the map includes randomly selecting at least one of the discrete parameterization values. In some embodiments, the steps of forming a map and measuring are carried out a first and second time and compared to each other or to a reference map to form a comparison measure. In some embodiments, steps of deriving one or more new input variables is based on the comparison measure. In some embodiments, the step of deriving includes a dimensionality reduction algorithm. In some embodiments, the dimensionality reduction algorithm is a multidimensional scaling (MDS) algorithm.

In some embodiments, the method further includes the step of associating the one or more derived input variables with the input variables. In some embodiments, the step of associating includes determining a functional relationship between each of the one or more derived input variables and the input variables. In some embodiments, the method further includes the step of associating the one or more derived input variables with a measured characteristic of the medical implant. In an exemplary embodiment, the method further including configuring the medical implant by selecting values of the one or more derived input variables to substantially optimize the performance of the medical implant.

In some embodiments, the step of configuring includes operation of a configuring device, the configuration device including user input means to allow a user to select values of the one or more derived input variables.

In some embodiments, the configuration device further includes a display displaying a view scape representing the one or more derived input variables, and wherein a user selects values of the one or more derived input variables by moving in the view scape by the user input means.

In some embodiments, the medical implant is a cochlear implant

As would be appreciated by a person skilled in the art, the steps of the present invention as described in connection with the embodiments disclosed herein may be embodied directly in hardware, in software module executed by a processor, or in a combination of the two.

Although a number of exemplary embodiments of the present invention have been described in the foregoing detailed description, it will be understood that the invention is not limited to the embodiment disclosed, but is capable of numerous rearrangements, modifications and substitutions without departing from the scope of the invention as set forth and defined by the following claims.

What is claimed is:

1. A method for determining a first set of one or more parameters for configuring a system having a multi-dimensional parameter-space, the method comprising:

evaluating a behavior of the system over a predetermined selection of parameter values for a second set of parameters, which includes selecting a plurality of discrete parameterization values spanning an input parameterization value range for each of the parameters in the second set, forming a first map by selecting a discrete parameterization value for each parameter in the second set to form a first total set of discrete parameterization values, measuring a characteristic of the system for the first map, forming a second map by selecting a discrete parameterization value for each parameter in the second set to form a second total set of discrete parameterization values, measuring the characteristic of the system for the second map, comparing the first map and the second map to each other or to a reference map to form a comparison measure; and deriving, based on the comparison measure and using a multidimensional scaling (MDS) algorithm, the first set of one or more parameters to configure the system based on the evaluated behavior of the system, wherein the number of parameters in the first set is fewer than the number of parameters in the second set.

2. The method of claim 1, wherein the step of forming the map includes:

randomly selecting at least one of the discrete parameterization values.

3. The method of claim 1, wherein the method further includes the step of associating the first set of one or more parameters with the second set of one or more parameters.

4. The method of claim 3, wherein the step of associating includes determining a functional relationship between each of the first set of one or more parameters and the second set of one or more parameters.

5. The method of claim 1, wherein the method further includes the step of associating the first set of one or more parameters with a measured characteristic of the system.

6. A method of reducing the input variables for configuring a medical implant that stimulates a physiological system according to external stimuli, the medical implant including a sensor to generate a sensed signal in accordance with the external stimuli, a processor for processing the sensed signal to generate a stimulation signal, the processor configured by a plurality of input variables adopting associated parameterization values, a stimulator for stimulating the physiological system in accordance with the stimulation signal, the method including:

evaluating by a recipient a behavior of the medical implant over a predetermined selection of the parameterization values, which includes selecting a plurality of discrete parameterization values spanning an input parameterization value range for each input variable, forming a first map by selecting a discrete parameterization value for each input variable to form a first total set of discrete parameterization values, measuring a characteristic of the medical implant for the first map, forming a second map by selecting a discrete parameterization value for each input variable to form a second total set of discrete parameterization values, measuring the characteristic of the medical implant for the second map, comparing the first map and the second map to each other or to a reference map to form a comparison measure; and deriving, based on the comparison measure and using a multidimensional scaling (MDS) algorithm, one or more new derived input variables to configure the medical implant based on the behavior of the medical implant as determined by the recipient, wherein the total number of the one or more new input variables is fewer than the number of input variables.

7. The method of claim 6, wherein the step of forming the map includes:

randomly selecting at least one of the discrete parameterization values.

8. The method of claim 6, wherein the method further includes the step of associating the one or more new derived input variables with the input variables.

9. The method of claim 8, wherein the step of associating includes determining a functional relationship between each of the one or more new derived input variables and the input variables.

10. The method of claim 6, wherein the method further includes the step of associating of the one or more new derived input variables with a measured characteristic of the medical implant.

11. The method of claim 10, further including configuring the medical implant by selecting values of the one or more new derived input variables to substantially optimize the performance of the medical implant.

12. The method of claim 11, wherein the step of configuring includes operation of a configuring device, the configuration device including user input means to allow a user to select values of the one or more new derived input variables.

13. The method of claim 12, wherein the configuration device further includes a display displaying a view scape representing the one or more new derived input variables, and wherein the user selects values of the one or more new derived input variables by moving in the view scape by the user input means.

14. The method of claim 13, wherein the medical implant is a cochlear implant.

* * * * *